US008717558B2

(12) United States Patent
Gu et al.

(10) Patent No.: US 8,717,558 B2
(45) Date of Patent: May 6, 2014

(54) LIQUID CORE PHOTONIC CRYSTAL FIBER BIOSENSORS USING SURFACE ENHANCED RAMAN SCATTERING AND METHODS FOR THEIR USE

(75) Inventors: Claire Gu, Santa Cruz, CA (US); Yi Zhang, Santa Cruz, CA (US); Chao Shi, Santa Cruz, CA (US); Jin Z. Zhang, Santa Cruz, CA (US); Leo Seballos, Saint Joseph, MN (US)

(73) Assignee: The Regents of the University of California, Oakland, CA (US)

( * ) Notice: Subject to any disclaimer, the term of this patent is extended or adjusted under 35 U.S.C. 154(b) by 694 days.

(21) Appl. No.: 12/733,492

(22) PCT Filed: Oct. 29, 2008

(86) PCT No.: PCT/IB2008/002872

§ 371 (c)(1), (2), (4) Date: Jan. 19, 2011

(87) PCT Pub. No.: WO2009/031033

PCT Pub. Date: Mar. 12, 2009

(65) Prior Publication Data

US 2011/0176130 A1 Jul. 21, 2011

Related U.S. Application Data

(60) Provisional application No. 60/967,555, filed on Sep. 4, 2007, provisional application No. 61/192,632, filed on Sep. 19, 2008.

(51) Int. Cl.
*G01J 3/44* (2006.01)

(52) U.S. Cl.
USPC .......... 356/301

(58) Field of Classification Search
USPC .......... 356/301
See application file for complete search history.

(56) References Cited

U.S. PATENT DOCUMENTS

2003/0172682 A1* 9/2003 Sato et al. .......... 65/393
2007/0020144 A1* 1/2007 Du et al. .......... 422/58

* cited by examiner

*Primary Examiner* — Tarifur Chowdhury
*Assistant Examiner* — Omar Nixon
(74) *Attorney, Agent, or Firm* — Matthew Kaser; Adam Warnick Bell; Bell & Associates

(57) ABSTRACT

The invention is drawn to a photonic crystal fiber that can be used with nanoparticles to detect and quantify components in a test sample. The invention further relates to methods of using the photonic crystal fiber for detecting chemical and biological analytes, and in use in optical communications.

2 Claims, 5 Drawing Sheets

Laser and Raman Spectrometer
Excitation light
Raman signal
R6G molecule
Fiber jacket
Silver Nanoparticle
Multimode Fiber

PCF with air holes

PCF with liquid core/ air cladding holes

LIQUID CORE PHOTONIC CRYSTAL FIBER BIOSENSORS USING SURFACE ENHANCED RAMAN SCATTERING AND METHODS FOR THEIR USE

The present application claims priority to U.S. Provisional Patent Application Ser. No. 60/967,555 entitled "Liquid Core Photonic Crystal Fiber Biosensors Using Surface Enhanced Raman Scattering And Methods For Their Use", filed Sep. 4, 2007, and U.S. Provisional Patent Application Ser. No. 61/192,632 entitled "Liquid Core Photonic Crystal Fiber Biosensors Using Surface Enhanced Raman Scattering And Methods For Their Use", filed Sep. 19, 2008, which are herein incorporated by reference in their entirety for all purposes.

This invention was made partly using funds from the United States' National Science Foundation grant number ECS-0401206 and ARP/UARC grant number NAS2-03144-TO.030.3MM.DGU-06. The United States Federal Government has certain rights to this invention.

TECHNICAL FIELD

The present invention relates to crystal fibers having a coating of particles comprising metallic nanoparticles having useful properties. The invention further relates to methods of using the crystal fibers for detecting chemical and biological analytes, and in use in optical communications.

BACKGROUND ART

During the 1980s Raman Scattering in fibers was demonstrated by Lin, Stolen, and other co-workers of AT&T Bell Laboratories in Holmdel, N.J. using Raman lasers operating between 0.3 to 2.0 μm. In the early years of the Raman fiber before extensive work had begun, no one perceived that a Raman fiber could be pumped by a practical semiconductor laser-based source or that an efficient CW-pumped Raman Fiber Laser was possible. However, with the development of Cladding-pumped Fiber Lasers and Fiber Bragg Gratings, diode-laser-based CW Raman Fiber Lasers have been made efficient, emitting at various wavelengths throughout the infrared spectrum a reality. (See van Gisbergen et al. (1996) Chem. Phys. Lett. 259: 599-604.)

Raman spectroscopy is a powerful optical technique for detecting and analyzing molecules. Its principle is based on detecting light scattered off a molecule that is shifted in energy with respect to the incident light. The shift, called Raman shift, is characteristic of individual molecules, reflecting their vibrational frequencies that are like fingerprints of molecules. As a result, the key advantage of Raman spectroscopy is its molecular specificity while its main limitation is the small signal due to low quantum yield of Raman scattering. One way to enhance the Raman signal is to tune the excitation wavelength to be on resonance with an electronic transition, so called resonance Raman scattering. This can usually produce an enhancement on the order of $10^2$-$10^3$ fold.

Another technique to enhance Raman scattering is surface enhancement by roughened metal surfaces, notably silver and gold, that provides an enhancement factor on the order of $10^6$-$10^8$. This is termed surface enhanced Raman scattering (SERS). Similar or somewhat larger enhancement factors (~$10^8$-$10^{10}$) have been observed for metal, mostly silver or gold, nanoparticles.

In the last few years, it has been shown that an even larger enhancement (~$10^{10}$-$10^{15}$) is possible for aggregates of metal nanoparticles (MNPs), silver and gold. The largest enhancement factor of $10^{14}$-$10^{15}$ has been reported for rhodamine 6G (R6G) on single silver nanoparticle aggregates. This huge enhancement is thought to be mainly due to significant enhancement of the local electromagnetic field of the nanoparticle aggregate that strongly absorbs the incident excitation light for the Raman scattering process. With such large enhancement, many important molecules that are difficult to detect with Raman normally can now be easily detected. This opens many interesting and new opportunities for detecting and analyzing molecules using SERS with extremely high sensitivity and molecular specificity.

SERS can also be developed into a molecular imaging technique for biomedical and other applications. Existing Raman imaging equipment should be usable for SERS imaging. SERS will provide a much-enhanced signal and thereby significantly shortened data acquisition time, making the technique practically useful for medical or other commercial and industrial applications including chip inspection or chemical monitoring. SERS is also useful for detecting other cancer biomarkers that can interact or bind to the MNP surface. For example, Sutphen et al. have recently shown that lysophospholipids (LPL) are potential biomarkers of ovarian cancer (Sutphen et al. (2004) Cancer Epidemiol. Biomarker Prev. 13: 1185-1191).

Photonic crystal fibers have been developed that can detect, identify, and quantify ultra small quantities of analytes in air and aqueous samples. In one example of the prior art, Du and Sukhishvili disclose a sensor comprising a photonic crystal fiber having an air hole cladding with functionalized air holes (Du and Sukhishvili, US Publication Number US 2007/0020144 A1, published 25 Jan. 2007). The photonic crystal fiber disclosed by Du and Sukhishvili comprises a solid core photonic crystal fiber; of note, Du and Sukhishvili described that "(c)omparison of FIG. 18 with FIG. 16 shows that the Ag nanoparticles 82 are present at a much lower density than the Ag nanoparticles 74 of the previous experiment. It is also apparent that the Ag nanoparticles 82 are much larger than the nanoparticles 74, and would, therefore, be less suitable for enhancement of SERS spectra" and that "(t)he moderate signals detected from adsorbed Rh6G (rhodamine 6G) in no salt aqueous solution were highly prone to fast photodegradation, and in a typical experiment, a SERS signal was not detectable after a 1 minute exposure of the substrate to 532 nm 10 mW laser radiation" (Du and Sukhishvili, paragraphs 59 and 52, respectively).

Others have also disclosed photonic crystal fibers, for example Konorov et al. (2005, Optics Express, 13: 3454-3459) and Konorov et al. (2006, Optics Lett., 31: 1911-1913). Konorov et al. (2005) disclose multicore hollow photonic crystal fibers of fused silica or soft glasses having inner diameters of the hollow core of about 2.5 μm and 3 μm or about 3 μm and 3.5 μm, respectively. Konorov et al. (2006) disclose hollow photonic crystal fibers with inner diameters of between about 8.6 μm and 9.5 μm and an outer diameter of 84 μm. Yan et al. also disclosed a novel hollow core photonic crystal fiber surface-enhanced Raman probe in Yan et al., (2006) (Yan et al. (2006) Appl. Phys. Lett. 89:204101).

The original single multimode SERS fiber probe was demonstrated in 1991 by Mullen et al. (Mullen and Carron (1991) Anal. Chem. 63: 2196). In the following years, studies involving different kinds of fiber tips were tested, such as flat, angled and tapered fibers (Viets and W. Hill (2000) J. Raman Spec. 31: 625; Viets and Hill (2001) J. Phys. Chem. B 105: 6330; and Viets and Hill (1998) Sens. Actuators B-Chem. 51: 92). Although they were easy to implement, the small number of SERS substrate particles in the active region limited the sensitivity of these sensors. In order to involve more particles in the SERS activity, hollow core photonic crystal fiber (HCPCF) and liquid core photonic crystal fiber (LCPCF) were tested recently (see Zhu et al. (2006) Opt. Exp. 14: 3541; Yan et al. (2006) Appl. Phys. Lett. 89: 204101; and Zhang et al. (2007) Appl. Phys. Lett. 90, 193504. High sensitivity, and low fiber SERS background show a promising future of PCF sensors. However, the wavelength sensitive nature of HCPCFs limits the application of a HCPCF to a single excitation wavelength and the cost of PCFs is still high. While normal fibers are lower in cost, their sensitivities are somewhat limited, often due to the background Raman scattering from the fiber itself. Therefore, it is highly desired to improve the detection sensitivity of SERS sensors based on conventional fibers. Fiber SERS sensors with high sensitivity, remote sensing capability, and low cost will find potential applications in medical, environmental, food detection, and toxin identification.

For many practical applications, for example SERS and optical fibers, it is highly desirable to narrow the distribution of size/shape of nanoparticle aggregates. For SERS in particular, the incident light has to be on resonance with the substrate absorption. Only those nanoparticle aggregates that have resonance absorption of the incident light are expected to be SERS active. It is thus extremely beneficial to have a narrow size/shape distribution and thereby narrow optical absorption.

Fluorescent nanoparticles (quantum dots (QDs) such as semiconductor quantum dots, SQDs) have been used recently as fluorescent biological markers and have been found to be extremely effective. They offer advantages including higher stability, stronger fluorescence, tunability of color, and possibility of optical encoding based on different sized or colored SQDs.

Metal nanoparticles have been recognized for their unique optical properties that could be exploited in optoelectronic devices. Nanoparticle systems composed of gold, for example, have distinct optical properties that make them amenable to study by Raman scattering. The Raman spectrum of the adsorbed species is significantly enhanced by 10 to 15 orders of magnitude when the metal nanoparticles have aggregated, leading to enhanced electromagnetic field effects near the surface that increases the Raman scattering intensity. The greater sensitivity found in the surface enhanced Raman scattering (SERS) of metal nanoparticle aggregates facilitates the detection and analysis of a whole host of molecules that were previously difficult to study.

Wang et al. disclose a method of using SQDs (dye-conjugated CdTe nanoparticles, CT-NPs) to detect interactive binding between Ag-CT-NPs and Ab-CT-NPs (Wang et al. (2002) NanoLett. 2: 817-822). The interactions were determined by differential quenching or enhancement fluorescence activity of two different sized SQDs (red or green) measured during the analysis.

The chemical methods used historically for the production of gold nanoparticle aggregates (GNAs) results in a wide distribution of aggregate size. This distribution leads to a broadened absorption spectrum. Accordingly, researchers have attempted to narrow the lineshape of the spectral peak due to the aggregates by homogenizing the size of the GNAs after they have been produced. By eliminating certain ranges of aggregate size, absorption spectrum peaks should narrow appreciably and concomitantly increase in intensity, resulting in more sensitive detection. Previous attempts to select for a narrow size range of aggregates have employed mechanical techniques such as passing a solution of aggregates through a filter. For example, Emory & Nie have employed size-selective fractionation using membrane filters to select for optically active silver nanoparticles (Emory and Nie, (1997) J. Phys. Chem. B, 102: 493-497).

The use of SERS for analyte detection of biomolecules has been previously studied. U.S. Pat. No. 6,699,724 to West et al. describes a chemical sensing device and method (nanoshell-modified ELISA technique) based on the enzyme-linked immunoadsorbant assay (ELISA). The chemical sensing device can comprise a core comprising gold sulfide and a surface capable of inducing surface enhanced Raman scattering (SERS). In much of the patent disclosure, the nanoparticle is disclosed as having a silica core and a gold shell. The patent discloses that an enhancement of 600,000-fold ($6\times10^5$) in the Raman signal using conjugated mercaptoaniline was observed.

In the nanoshell-modified ELISA technique, antibodies are directly bound to the metal nanoshells. Raman spectra are taken of the antibody-nanoshell conjugates before and after the addition of a sample containing a possible antigen, and binding of antigen to antibody is expected to cause a detectable shift in the spectra.

The conjugation of quantum dots to antibodies used for ultrasensitive nonisotopic detection for use in biological assays has also been studied. U.S. Pat. No. 6,468,808 B1 to Nie et al. disclosed an antibody is conjugated to a water-soluble quantum dot. The binding of the quantum dot-antibody conjugate to a targeted protein will result in agglutination, which can be detected using an epi-fluorescence microscope. In addition, Nie et al. described a system in which a quantum dot is attached to one end of an oligonucleotide and a quenching moiety is attached to the other. The preferred quenching moiety in the Nie patent is a nonfluorescent organic chromophore such as 4-[4'-dimethylaminophenylazo]benzoic acid (DABCYL).

Raman amplifiers are also expected to be used globally as a key device in next-generation optical communications, for example, in wavelength-division-multiplexing (WDM) transmission systems. Raman scattering occurs when an atom absorbs a photon and another photon of a different energy is released. The energy difference excites the atom and causes it to release a photon with low energy; therefore, more light energy is transferred to the photons in the light path.

There is therefore a need in the art for use in the biomedical analytical industries and the optical communications industries to provide more sensitive compositions and devices that are inexpensive to manufacture and easy to use.

DISCLOSURE OF THE INVENTION

The invention provides a photonic crystal fiber, methods for manufacture and/or fabrication of said a photonic crystal fiber, and methods for using the photonic crystal fiber. The photonic crystal fiber is used as a sensor for any analyte and is many times more sensitive than sensors in current use, an unexpected property. The photonic crystal fiber is used to measure the surface enhanced Raman scattering (SERS) resulting from interactions between the components of the photonic crystal fiber and the analyte of interest.

In one embodiment, the invention provides a photonic crystal fiber having improved sensitivity for detecting and/or sending a chemical, the fiber comprising a proximal end, a distal end, the ends defining a lumen, an outer surface, and an inner surface. In one embodiment, the inner surface further comprises, in part, a metallic nanoparticle composition. In an alternative embodiment, the outer surface further comprises, in part, a metallic nanoparticle composition. In one preferred embodiment the photonic crystal fiber has a cylindrical shape and an approximately circular cross-section. In another preferred embodiment the photonic crystal fiber is flexible. In one preferred embodiment the lumen of the fiber further comprises a liquid and/or a gas. In another preferred embodiment the lumen of the fiber comprises a solid composition. In one embodiment of the photonic crystal fiber, the metallic nanoparticle composition comprises a double substrate sandwich structure. In an alternative embodiment, the metallic nanoparticle composition comprises a single layer. In another alternative embodiment, the metallic nanoparticle composition comprises a plurality of layers.

In one embodiment the sensitivity is enhanced by at least 10 times. In another embodiment, the sensitivity is enhanced by at least 25 times. In another embodiment the sensitivity is enhanced by at least 50 times. In another embodiment, the sensitivity is enhanced by at least 75 times. In another embodiment the sensitivity is enhanced by at least 100 times. In another embodiment, the sensitivity is enhanced by at least 200 times. The sensitivity can be enhanced by, for example, up to 10 times, up to 15 times, up to 20 times, up to 25 times, up to 30 times, up to 35 times, up to 40 times, up to 45 times, up to 50 times, up to 55 times, up to 60 times, up to 65 times, up to 70 times, up to 75 times, up to 80 times, up to 85 times, up to 90 times, up to 95 times, up to 100 times, up to 150 times, up to 200 times, up to 250 times, up to 300 times, up to 350 times or more, or any similar level thereabouts.

In an alternative embodiment, the photonic crystal fiber further comprises a plurality of lumens and wherein each end of the fiber comprises a plurality of apertures to each lumen.

In one alternative preferred embodiment the photonic crystal fiber is solid.

In another embodiment, the metallic nanoparticle composition comprises a metal, wherein the metal is selected from the group consisting of can be gold, silver, platinum, copper, aluminum, palladium, cadmium, iridium, and rhodium. In a more preferred embodiment the metal is silver. In a most preferred embodiment, the metallic nanoparticle composition comprises silver citrate.

In one embodiment, the cross-section of the photonic crystal fiber has dimensions of about between 0.1 μm and 100 μm. For example, the cross-section of the photonic crystal fiber can be about 0.1 μm, 0.2 μm, 0.3 μm, 0.4 μm, 0.5 μm, 0.6 μm, 0.7 μm, 0.8 μm, 0.9 μm, 1 μm, 2 μm, 3 μm, 4 μm, 5 μm, 6 μm, 7 μm, 8 μm, 9 μm, 10 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, or any dimension therebetween. In another embodiment, the length of the photonic crystal fiber has dimensions of about between 0.5 cm and 100 cm. For example, the length of the photonic crystal fiber can be about, 0.5 cm, 0.6 cm, 0.7 cm, 0.8 cm, 0.9 cm, 1 cm, 2 cm, 3 cm, 4 cm, 5 cm, 6 cm, 7 cm, 8 cm, 9 cm, 10 cm, 12 cm, 13 cm, 14 cm, 15 cm, 16 cm, 17 cm, 18 cm, 19 cm, 20 cm, 25 cm, 30 cm, 35 cm, 40 cm, 45 cm, 50 cm, 55 cm, 60 cm, 65 cm, 70 cm, 75 cm, 80 cm, 85 cm, 90 cm, 95 cm, 100 cm, or any dimension therebetween. In another embodiment, the cross-section of the lumen of the photonic crystal fiber has dimensions of about between 0.1 μm and 100 μm. For example, the cross-section of the lumen of the photonic crystal fiber can be about 0.1 μm, 0.2 μm, 0.3 μm, 0.4 μm, 0.5 μm, 0.6 μm, 0.7 μm, 0.8 μm, 0.9 μm, 1 μm, 2 μm, 3 μm, 4 μm, 5 μm, 6 μm, 7 μm, 8 μm, 9 μm, 10 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, or any dimension therebetween.

The photonic crystal fiber is particularly useful for sensing and measuring the quantities of an analyte. The photonic crystal fiber disclosed herein is an improvement over the prior art in that the presence of a fluid or liquid detection in the lumen of the photonic crystal fiber results in an unexpectedly superior enhancement factor of the SERS signal from the photonic crystal fiber and a test sample comprising the analyte of interest. In a preferred embodiment the analyte is a biological composition. The biological composition can be, for example, a protein, a peptide, a polyketide, an antibody, an antigen, a nucleic acid, a peptide nucleic acid, a sugar, a lipid, a glycophosphoinositol, and a lipopolysaccharide. In another alternative embodiment the analyte can be an explosive, a chemical and/or biological warfare agent, a toxin, a virus particle, and a biological cell.

In yet a further embodiment, the photonic crystal fiber comprises a support. In a preferred embodiment, the support comprises a medium that is permeable to an analyte of interest. In one embodiment the support can be a gel, a solid, or a liquid. The support can comprise a synthetic composition, such as, but not limited to a polymer, a block co-polymer, a random copolymer, a carbon composite material, a metal composite material, or the like. Alternatively, the support can comprise a biological compound, such as, but not limited to, a starch composition, a cellulose composition, a collagen composition, a latex composition, a protein, a polypeptide, a carbohydrate, a sugar, a mixture thereof, or the like. In another alternative, the support can be a liquid or a gel-phase composition, such as, but not limited to, an aqueous composition, an alcohol composition, a hydrogel, a mixture thereof, or the like. The support can be in the form of a matrix, a crystalline structure, a cross-linked polymer, a porous composition, or the like. Such structures, materials, and compositions are well known to those of skill in the art.

In another preferred embodiment, the photonic crystal fiber has a surface wherein the surface can induce surface enhanced Raman scattering (SERS).

In still another preferred embodiment, the photonic crystal fiber further comprises at least one detecting molecule, wherein the detecting molecule is bound to the surface or support. In a more preferred embodiment the detecting molecule is selected from the group consisting of proteins, peptides, antibodies, antigens, nucleic acids, peptide nucleic acids, sugars, lipids, glycophosphoinositols, and lipopolysaccharides.

In a yet more preferred embodiment the detecting molecule is an antibody. In another preferred embodiment, the detecting molecule is an antigen.

In another embodiment, the invention provides a photonic crystal fiber further comprising at least one semiconductor quantum dot. In a preferred embodiment the semiconductor quantum dot further comprises a linker molecule, the linker molecule selected from the group consisting of a thiol group, a sulfide group, a phosphate group, a sulfate group, a cyano group, a piperidine group, an Fmoc group, and a Boc group.

In a still further embodiment, the invention provides a photonic crystal fiber comprising at least one semiconductor quantum dot wherein the semiconductor quantum dot further comprises a detecting molecule, wherein the detecting molecule is bound to the semiconductor quantum dot. In a more preferred embodiment, the detecting molecule is selected from the group consisting of proteins, peptides, antibodies, antigens, nucleic acids, peptide nucleic acids, sugars, lipids, glycophosphoinositols, and lipopolysaccharides.

In a more preferred embodiment, the detecting molecule is an antibody. In the alternative, a more preferred embodiment comprises a chemical sensing device wherein the detecting molecule is an antigen.

The invention further provides a method for sensing an analyte in a test sample, the method comprising the steps of:

(i) providing the photonic crystal fiber disclosed herein; (ii) providing a test sample; (iii) immersing the photonic crystal fiber in the test sample; (iv) irradiating the photonic crystal fiber and the test sample with an excitation light, the excitation light having a wavelength in the visible to near infra-red (near-IR) portion of the spectrum, such as, for example, from between about 600 nm to about 1,400 nm, from between about 620 to about 1,000 nm, from between about 650 to about 950 nm, from between about 700 nm to about 900 nm, from between about 750 nm to about 880 nm, or from between about 770 nm to about 800 nm; (v) measuring the Raman spectrum of a photonic crystal fiber and a control sample, thereby determining the background Raman spectrum; (vi) detecting the surface enhanced Raman scattering (SERS) signal emitted from the photonic crystal fiber and the test sample; (vii) measuring the Raman spectrum of the photonic crystal fiber and the test sample, thereby determining the analyte Raman spectrum; subtracting the background Raman spectrum from the analyte Raman spectrum, thereby determining the quantity of the analyte in the sample; (viii) determining the enhancement factor of the SERS signal from the control sample; (ix) determining the enhancement factor of the SERS signal from the test sample; wherein the enhancement factor of the SERS signal from the test sample is at least 100-fold compared with a SERS signal from the control sample, the method resulting in sensing the analyte. In a preferred embodiment, the analyte is a biological composition. In a more preferred embodiment, the biological composition is selected from the group consisting of a protein, a peptide, a polyketide, an antibody, an antigen, a nucleic acid, a peptide nucleic acid, a sugar, a lipid, a glycophosphoinositol, and a lipopolysaccharide. In an alternative more preferred embodiment, the analyte is selected from the group consisting of an explosive, a chemical warfare agent, a biological warfare agent, a toxin, a virus particle, and a biological cell.

The invention further provides a method for measuring the quantity of an analyte in a test sample, the method comprising the steps of: (i) providing the photonic crystal fiber disclosed herein; (ii) providing a test sample; (iii) immersing the photonic crystal fiber in the test sample; (iv) irradiating the photonic crystal fiber and the test sample with an excitation light, the excitation light having a wavelength in the visible to near infra-red (near-IR) portion of the spectrum, such as, for example, from between about 600 nm to about 1,400 nm, from between about 620 to about 1,000 nm, from between about 650 to about 950 nm, from between about 700 nm to about 900 nm, from between about 750 nm to about 880 nm, or from between about 770 nm to about 800 nm; (v) measuring the Raman spectrum of a photonic crystal fiber and a control sample, thereby determining the background Raman spectrum; (vi) detecting the surface enhanced Raman scattering (SERS) signal emitted from the photonic crystal fiber and the test sample; (vii) measuring the Raman spectrum of the photonic crystal fiber and the test sample, thereby determining the analyte Raman spectrum; subtracting the background Raman spectrum from the analyte Raman spectrum, thereby determining the quantity of the analyte in the sample; (viii) determining the enhancement factor of the SERS signal from the control sample; (ix) determining the enhancement factor of the SERS signal from the test sample; wherein the enhancement factor of the SERS signal from the test sample is at least 100-fold compared with a SERS signal from the control sample, the method resulting in measuring the quantity of the analyte. In a preferred embodiment, the analyte is a biological composition. In a more preferred embodiment, the biological composition is selected from the group consisting of a protein, a peptide, a polyketide, an antibody, an antigen, a nucleic acid, a peptide nucleic acid, a sugar, a lipid, a glycophosphoinositol, and a lipopolysaccharide. In an alternative more preferred embodiment, the analyte is selected from the group consisting of an explosive, a chemical warfare agent, a biological warfare agent, a toxin, a virus particle, and a biological cell. In one preferred embodiment the wavelength of the excitation light is about 633 nm. In another alternative preferred embodiment the wavelength of the excitation light is about 785 nm.

Another embodiment of the invention provides a method for detecting an analyte in a sample using a photonic crystal fiber, the method comprising the steps of: i) providing a sample; ii) providing a semiconductor quantum dot comprising a linker molecule (LM-SQD); iii) conjugating the analyte in the sample with the LM-SQD thereby producing an analyte-LM-SQD conjugate; iv) providing a photonic crystal fiber comprising a plurality of particles, each particle comprising: a shell having at least one surface and a lumen and wherein the shell comprises a sulfur-oxygen molecular species, and the shell surface further comprising a detecting molecule; v) incubating the analyte-LM-SQD conjugate with the photonic crystal fiber for a predetermined time period; and vi) measuring the extent of binding between the analyte-LM-SQD conjugate and the photonic crystal fiber; thereby detecting the analyte in the sample.

In a yet additional embodiment, the invention provides an optical communications device comprising a photonic crystal fiber, a plurality of particles, each particle comprising: a shell having at least one surface and a lumen.

In a more preferred embodiment the optical communications device comprises a fiber, wherein the fiber is selected from the group consisting of ceramics, glasses, polymers, and metal-polymer composites. In another preferred embodiment the chemical sensor is disposed upon a surface of the fiber.

The invention also provides a process for fabricating a photonic crystal fiber, the method comprising the steps of (i) mixing $AgNO_3$ with ethanol; (ii) stirring the $AgNO_3$ in ethanol until the $AgNO_3$ is dissolved in the ethanol; (iii) adding three molar equivalents of hexanethiol to the solution; (iv) adding toluene to the solution; (v) reducing the solution using a ten-fold molar excess of $NaBH_4$ dissolved in nanopure water; (vi) washing the solution at least three times with nanopure water thereby removing inorganic impurities; (vii) collecting the toluene phase; (viii) evaporating the toluene phase, thereby causing metallic nanoparticles to come out of solution; (ix) collecting the metallic nanoparticles; (x) dissolving the metallic nanoparticles in methanol; (xi) evaporating the methanol; (xii) collecting the metallic nanoparticles; re-dissolving the metallic nanoparticles in methanol; (xiii) providing a crystal fiber, the crystal fiber having a proximal end and a distal end; (xiv) dipping the distal end of the crystal fiber into the metallic nanoparticle solution; (xv) removing the distal end of the fiber from the metallic nanoparticle solution; (xvi) washing the distal end of the crystal fiber with ethanol; (xvi) drying the distal end of the crystal fiber using a gas; (xvii) irradiating the crystal fiber with ultra-violet radiation; (xviii) repeating steps (xiv) through (xvii) at least once; the process thereby fabricating a photonic crystal fiber. In one preferred embodiment the metallic nanoparticles are hexanethiolate-protected silver (AgC6) nanoparticles.

BRIEF DESCRIPTION OF THE DRAWINGS

FIG. 3 shows representative spectra of a hollow core photonic crystal fiber.

FIG. 7*a*, $10^{-5}$ M; 7*b*, $10^{-6}$ M; 7*c*, $10^{-7}$ M; 7*d*, $10^{-8}$ M; and 7*e*, $10^{-9}$ M.

FIG. 7*f* illustrates data from FIGS. 7*a-e* showing a plot of SERS intensity versus R6G concentration using the peak 1514.3 $cm^{-1}$ as an example for three detection methods (TC-MMF, MMF in sample solution, and direct detection).

MODE(S) FOR CARRYING OUT THE INVENTION

Figure 1:
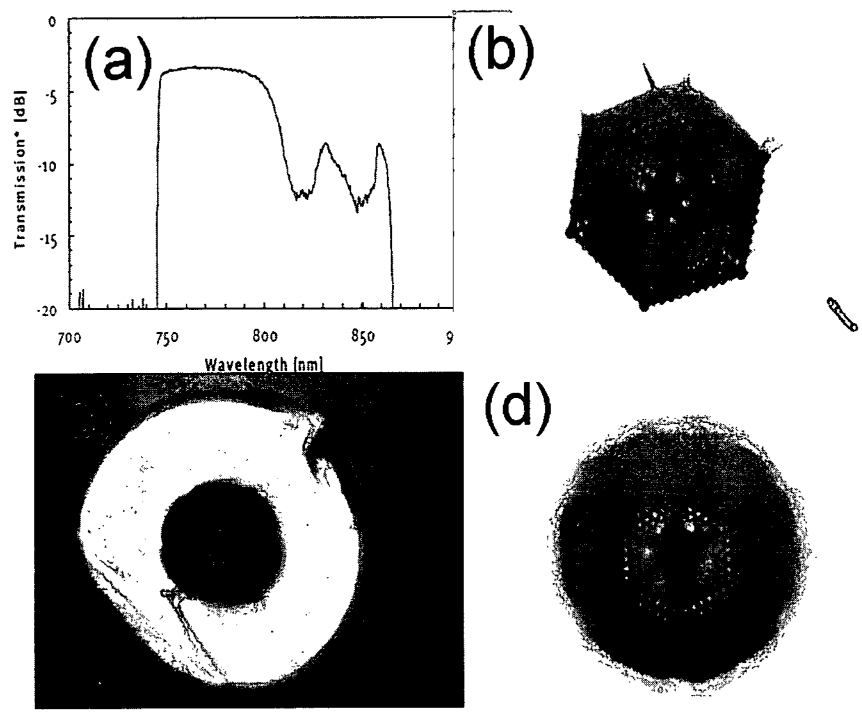
FIG. 1*a* shows the transmission spectrum of the Air-6-800 photonic crystal fiber.
FIG. 1*b* shows a micrograph of the cross section of a hollow core photonic crystal fiber (HCPCF).
FIG. 1*c* shows the probing tip of a HCPCF after post-fabrication processing.
FIG. 1*d* is an enlarged view of FIG. 1*c*.

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "a particle" includes a plurality of such particles, and a reference to "a surface" is a reference to one or more surfaces and equivalents thereof, and so forth.

The invention provides a photonic crystal fiber and methods for fabricating a hollow photonic crystal fiber (HCPCF) and a liquid core photonic crystal fiber (LCPCF) and demonstrates using the SERS sensor for in vitro molecular detection.

In another embodiment the invention provides a crystal fiber having a configuration based on a double-substrate "sandwich" structure (DSSS) that is designed to enhance the SERS activity using two substrates simultaneously.

Liquid Core Photonic Crystal Fiber Sensor Based on Surface Enhanced Raman Scattering Surface enhanced Raman scattering (SERS) sensors based on optical fibers have attracted significant interest in molecule sensing. On one hand, SERS offers rich molecular information while amplifying the signal by orders of magnitude (~$10^9$). On the other hand, the flexibility of optical fibers makes it an ideal SERS platform for practical applications. Previously, fibers with different configurations such as a flat, angled, or tapered tip were tested as SERS platforms. The main limitation has been the small number of SERS substrate particles on the active fiber region, requiring high laser intensities and/or long integration times to attain reasonable SERS spectra.

To overcome this hurdle, several types of photonic crystal fibers were suggested and tested. Previously, SERS was reported with the gold nanoparticles and analyte coated (dried) on the inner surface of the air holes of a hollow core photonic crystal fiber (HCPCF) with the excitation light coupled into the opposite end. Although the active sensing area was significantly increased, the HCPCF SERS sensor performed well when the nanoparticles/analyte dried along the light path. If the HCPCF were dipped directly into the sample solution, the central hole, along with the surrounding cladding holes, would all be filled with solution, leading to a reduction of the refractive index contrast inside and outside the holes, therefore, losing the photonic bandgap. This would in turn result in the loss of light confinement and limit in vivo and in vitro applications of as a HCPCF SERS sensor. The cladding holes of the HCPCF (model Air-6-800 or model HC-633-01 fibers, for example; other suitable fibers may also be used) were alternatively sealed using a fusion splicer. Heat from the two electric tips of the fusion splicer sealed the cladding holes leaving the central core of the fiber open.

The invention provides methods, system, and apparatus to fabricate an ultra-sensitive chemical and biological sensor based on surface enhanced Raman scattering and a novel liquid core photonic crystal fiber (LCPCF). Surface enhanced Raman scattering provides the fingerprint of the analyte molecules and enlarges or amplifies the signal by up to at least $10^{15}$ times that of regular Raman signals. The sensor can be used for in vivo and in vitro detection and sensing if a flexible LCPCF probe is used. With this novel fiber architecture, LCPCF achieved a much greater interaction volume compared with a regular solid core multimode fiber, due, in part, to both the photonic bandgap guiding and the index guiding mechanisms; hence, a highly improved sensitivity with an additional enhancement of at least one hundred times.

A Double Substrate "Sandwich" Structure for Fiber Surface Enhanced Raman Scattering Detection The invention provides methods, systems, and apparatus to fabricate an ultra-sensitive chemical and biological sensor based on a novel liquid core photonic crystal fiber (LCPCF) with silver nanoparticles (SNPs) coated on the inner wall of the fiber core and surface enhanced Raman scattering (SERS). Surface enhanced Raman scattering provides the fingerprint of the analyte molecules and enlarges its signals by up to $10^{15}$ times that of regular Raman signals and the flexible LCPCF probe makes the sensor applicable for in vivo and in vitro detection. At the same time, the SNPs on the inner wall can induce extra stronger electromagnetic field enhancement due to the "sandwich" structure, which can result in higher sensitivity. The analyte molecules are sandwiched between two SNPs. One is coated on the inner wall and another is in the solution with the molecules absorbed on it. As the simulation shows, the electromagnetic field can be stronger between two closely placed SNPs, thereby indicating that the stronger electromagnetic field can result in higher SERS signal. This novel fiber architecture comprising an inner wall coated LCPCF achieved a much greater sensitivity up to at least ten times better than the uncoated LCPCF model (regular solid core multimode fiber).

In one embodiment, a configuration based on a double-substrate "sandwich" structure (DSSS) was designed to enhance the SERS activity using two substrates simultaneously. One simple approach to achieve this was to coat one SERS substrate, for example, silver nanoparticles (SNPs), on the tip of a multimode fiber (MMF) and mix second substrate in solution with the target analyte molecules. Upon dipping the coated fiber probe into the solution, randomly formed structures of the two substrates sandwich the analyte molecules in between. While this approach does not generate controllable sandwich structures, it is easy to implement. Perfect "sandwich" structures would be expected to show stronger enhancement than such random structures.

As shown in Xu and Kall's simulation (Xu and Kall, 2002), the electromagnetic field between two closely spaced silver nanoparticles was substantially enhanced by an order of $10^{11}$ in hot nanojunctions. (See Xu and Kall (2002) Phys. Rev. Lett. 89: 246802; Xu et al. (2000) Phys. Rev. E 62: 4138). Based on this huge enhancement, "sandwich" structures have the potential to reach greatly improved SERS sensitivity when the analyte molecules are placed between two metal substrate nanostructures.

Figure 5:
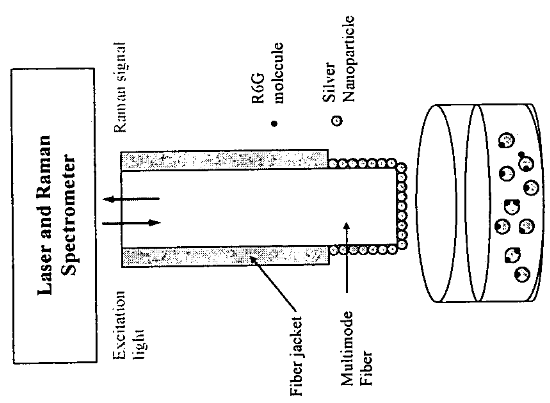
FIG. 5 is a schematic of the tip coated multimode fiber sensor.
Figure 7:
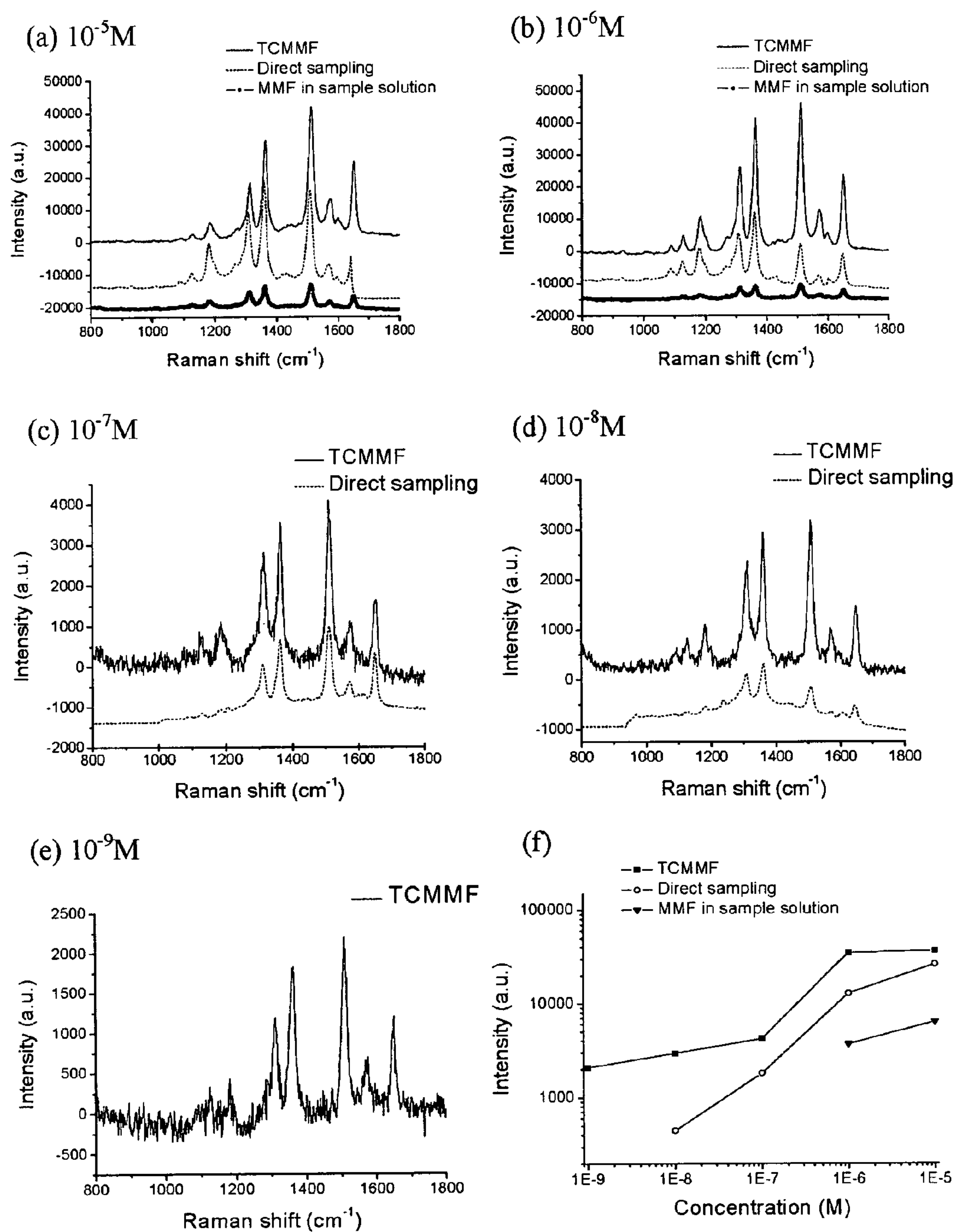
FIG. 7 shows SERS spectra of R6G molecules at various concentrations using different detection methods (TCMMF, MMF in sample solution, and direct detection). The concentrations of the R6G molecules are as follows.

There are different approaches to implement such a "sandwich" structure. One simple scheme is shown in FIG. 5 based on a tip coated multimode fiber (TCMMF). The excitation light for SERS is focused into the MMF from one end and well confined in the fiber during the propagation to the far end of the fiber where most light will be absorbed by the SERS substrate, SNPs, coated onto the fiber tip and form a strong field around the tip. The sample solution is a mixture of the analyte molecules, for example, R6G, and SNPs with the molecules adsorbed on the nanoparticle surface. When the coated tip dips into the solution, the SNPs and analyte molecules in the solution interact and bind to the SNPs coated on the fiber tip. Statistically, some of the molecules are sandwiched in the junction between the two SNPs substrates, where the electromagnetic field is further enhanced leading to stronger SERS signals. The SERS signal from the sample propagates back from the MMF and photons are detected by the Raman spectrometer.

SERS can also be developed into a molecular imaging technique for biomedical and other applications. Exciting Raman imaging equipment may be usable for SERS imaging. SERS can provide an enhanced signal and thereby significantly shortened data acquisition time, making the technique practically useful for medical or other commercial and industrial applications including, but not limited to, chip inspection or chemical monitoring.

SERS for Raman Amplifier in Optical Communications

Raman amplifiers have been used to amplify signal in optical communications. SERS can provide more amplification than normal Raman amplifiers. By coating nanoparticle compositions onto or into glass or polymer fibers, Raman scattering from the glass or polymer matrix can be used to amplify optical signal with the proper wavelength.

Detection of Specific Compounds Using Fibers

The nanoparticle compositions can be used to detect specific compounds that may be at very low levels in a sample. Such a sample can be blood, urine, saliva, lung lavage, gastric fluid, lymphatic fluid, any other body fluid, or the like. In addition, the sample can be a sample of water or other aqueous medium, such as water from a spring, a stream, a river, a pond, a lake, a sea, or an ocean. The sample can be a geological sample such as from a geothermal spring, a lava evaporate or exudate, a hydrocarbon, or from an abyssal trench; a plant sample such as from the xylem or phloem of a stalk or trunk; a sample from a fluid in a man-made structure such as concrete, cement, aggregate, or the like; a sample of fluid from a piece of machinery such as an engine, motor, compressor, or the like.

The nanoparticle composition can be conjugated with antibody, the antibody having been synthesized to bind a specific compound. Such a specific compound can be a protein, a fatty acid, a carbohydrate, an organic compound based upon a benzene ring structure, an organic compound based upon a short chain hydrocarbon, a medium chain hydrocarbon or a long chain hydrocarbon. The specific compound can be modified with a reactive group. Such reactive groups are well known to those of skill in the art and can include phosphate groups, methyl groups, hydroxyl groups, sulphate groups, acetyl groups, or the like.

The resulting substrate surface can have a surface area that is up to at least about 8,000-fold larger than the distal end surface of the original fiber. The diameter of the fiber can be from between about 0.01 μm to about 10 μm. In one alternative, the diameter is from between about 0.1 μm to about 1 μm. In another alternative, the diameter is between about 0.2 μm to about 8 μm.

The nanoparticle composition coating is applied and incorporated onto the substrate surface and light is directed longitudinally through the fiber. The light can be coherent and/or non-coherent. The light interacts with the nanoparticle aggregate-antibody conjugate complex and a resulting SERS profile can be compared with a SERS profile from the nanoparticle aggregate-antibody conjugate complex that is bound with a known amount of specific compound. The SERS radiation is detected using a photon detector suitably disposed to detect the SERS radiation. The detector can be disposed at or near the substrate surface of the fiber at the distal end or distal section of the fiber, at or near the proximal end or proximal section of the fiber, or at another position as disclosed herein.

The fiber can have one or more such substrate surfaces. In the case of two substrate surfaces, the second substrate surface can reflect the SERS signal from the first substrate surface to the detector longitudinally along the length of the fiber, resulting in a markedly improved amplification of the SERS signal. Similarly, the first substrate surface can reflect a SERS signal from the second substrate surface to the detector.

In another alternative, at least one additional fiber can be positioned in proximity to the distal end or distal section of the fiber. The end of the additional fiber can have the same shape as the shape of the distal end or distal section of the fiber, such that SERS radiation emitted from the fiber is conducted through the additional fiber to a detector. Two additional fibers can be used in parallel where there are two new substrate surfaces on the fiber.

The fiber can additionally have a non-uniform diameter, for example, the distal end having a cross-section perpendicular to the longitudinal plane that is larger in magnitude than a cross-section of the proximal end. Such a shape can further increase the amount of SERS radiation produced by a photon source.

The fiber can be made using glass, ceramics, or the like; or a polymeric compound such as cyclic olefin polymer (COP), polysulfone (for example, UDEL and RADEL resins), fluorinated terpolymers (such as those synthesized from tetrafluoroethylene, hexafluoropropylene, and vinylidene fluoride), polycarbonate, polyacrylate, polystryrene, or the like.

The SERS radiation can be further enhanced approximately 4-5-fold if an electrical field of a few Volts per centimeter (V/cm) is applied across the fiber, approximately perpendicular to the substrate surface. The potential difference can be maintained through an electrically conducting solution. The electrically conducting solution can be aqueous or non-aqueous but should not quench SERS radiation to the extent that the SERS enhancement due to the electrical field is quenched by the electrically conducting solution.

In one embodiment, a method to fabricate the LCPCF has been developed. The LCPCF sensor based on SERS has been demonstrated in the detection of molecules including R6G, human insulin, and tryptophan. With all the holes in a HCPCF filled with liquid samples, only the R6G SERS signal could be detected. However, using the LCPCF with only the hollow core filled with liquid samples, both human insulin and tryptophan SERS signals were easily detected besides R6G. This is attributed to confinement of both light and sample in the central core of the LCPCF and thereby increased interaction volume. Comparison between SERS signals measured with an LCPCF and by directly focusing the excitation light on a sample dried on a crystal substrate has indicated an enhancement factor of 100 for LCPCF. Theoretical analysis has verified the light confinement in an LCPCF.

In another embodiment, a unique double substrate sandwich structure based on TCMMF has been developed as a highly sensitive SERS probe. This probe is tested using R6G molecules and the sensitivity has been found to be 10 times better than that using a single SNPs substrate in solution. Concentration as low as $10^{-9}$ M can be readily detected using this probe, which is not possible using one of the two single substrates alone. The improvement of SERS sensitivity is attributed to the extremely large electromagnetic enhancement between SNPs. These experiments demonstrate the potential of using such a "sandwich" configuration for chemical and biological sensing and detection applications.

EXAMPLES

The invention will be more readily understood by reference to the following examples, which are included merely for purposes of illustration of certain aspects and embodiments of the present invention and not as limitations.

Example I

Synthesis of Liquid Core Photonic Crystal Fiber Sensor

Here we describe an exemplary method developed to fabricate a liquid core photonic crystal fiber (LCPCF) and demonstrate the potential of using the LCPCF SERS sensor for in vitro molecular detection. The LCPCF was fabricated by sealing the cladding holes of a hollow core photonic crystal fiber (HCPCF) while leaving the central core channel open to the outside, then dipping the processed tip into a solution of silver nanoparticles/analyte to fill the core by the capillary action. The HCPCF was purchased from Newport (Photonic Crystal Fiber, Model Air-6-800) (Newport Corporation, Irvine, Calif.). The fiber possessed a good band gap for the excitation wavelength (785 nm) that made it suitable for biomolecular sensing applications (see FIG. 1*a*). The HCPCF was cut into segments of ~10 cm in length, with both ends cleaved carefully (FIG. 1*b*). The cladding holes were sealed by exposing 2-3 mm of one tip of the well cleaved HCPCF into a high temperature flare (~1000° C.) for 3-5 seconds. For a piece of well processed HCPCF, one could see that only the surrounding cladding holes were closed and the central hollow core was still left open, as desired (FIG. 1*c*). After annealing, the processed fiber tip (probing tip) was cooled down for about 5 min then dipped into the solution containing both the SERS substrate and the analyte for 5 seconds to allow the solution to fill the hollow cores by ~1 cm via capillary action, therefore, only the central hole is filled with the liquid sample making it a LCPCF. The fiber was then lifted out and mounted on the microscope with the measuring tip under the objective focus.

Figure 2:
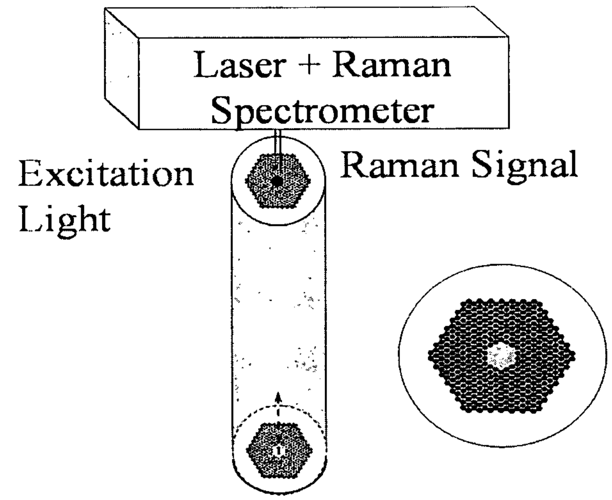
FIG. 2 is a schematic of a liquid core photonic crystal fiber (LCPCF) SERS sensor and its cross-sectional view. The spectrometer above the surface contains a CCD detector, a monochromator, and electronics for data collection.

As shown in FIG. 2, the excitation light was coupled in from the unprocessed end (measuring tip) of the LCPCF and was well confined in the core during the propagation. After interacting with the nanoparticles/analytes solution, the SERS signal from the sample propagated back to the measuring tip and was then collected through the objective lens into the Raman spectrometer. Sample measurements were obtained using a 785 nm diode laser coupled into the fiber through a Renishaw micro-Raman spectrometer with a Leica microscope and 50× objective lens. Ideally, the excitation beam should propagate in the core of the fiber. However, the beam's elliptical shape and size of ~200 $\mu m^2$ was much larger than the radius of the fiber core (a=3 μm).

Figure 3A:
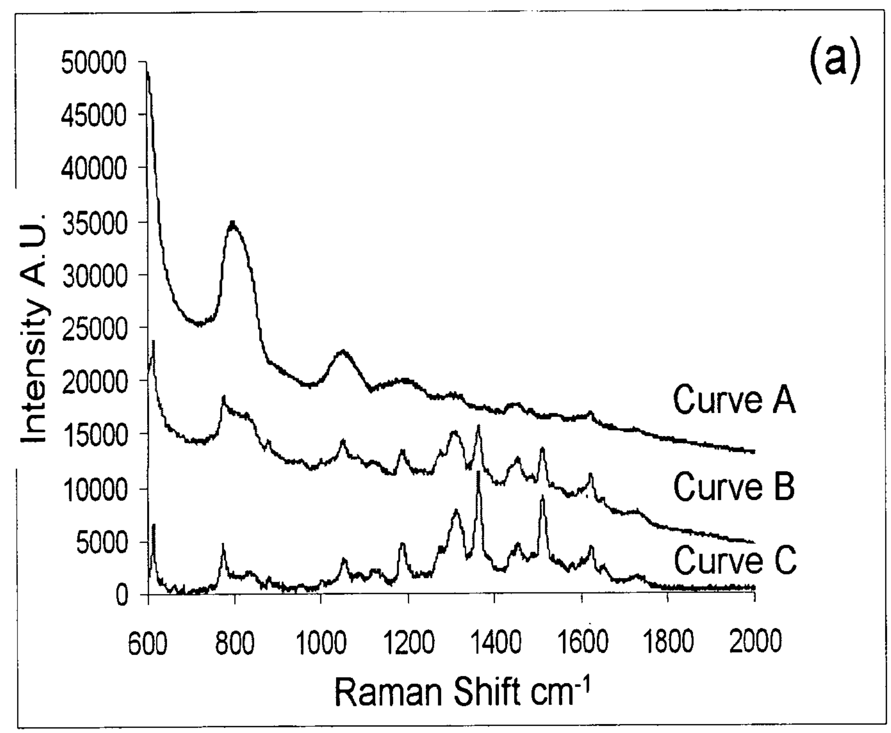
FIG. 3*a*, curve A: Background Raman spectrum of the HCPCF. Curve B: rhodamine 6G (R6G) Raman spectrum obtained using a HCPCF SERS probe without the post-fabrication processing; the HCPCF was dipped into the nanoparticle/R6G solution, Curve C: Subtraction of curve A from curve B showing the net R6G Raman signal.

Before using the HCPCF for measuring SERS spectrum of molecules, its Raman spectrum was obtained and presented as the inset in FIG. 3*a*, curve A. The spectrum is the same as that of a conventional silica fiber with solid core.

Silver nanoparticles, used as the SERS substrate, were synthesized using a citrate reducing agent. The UV-Vis of the nanoparticles has broad plasmon band in the 420 nm region indicates the presence of mainly individual silver nanoparticle that have a broad size/shape distribution and the TEM images verified that the size of the nanoparticle varies between 40 and 60 nm. Silver nitrate and sodium citrate were both purchased from Fisher Scientific. R6G, human insulin and tryptophan solutions (Sigma-Aldrich, St Louis, Mo.) were prepared and then mixed with the nanoparticles to test the LCPCF SERS probe's sensitivity. The final concentrations of the samples were ~$10^{-4}$-$10^{-5}$ M. Samples with similar concentration has been detected before by other researchers, however, difference types of SERS substrate, laser excitation wavelength and power were used, which makes the quantitative comparison more difficult and unavailable.

Figure 3B:
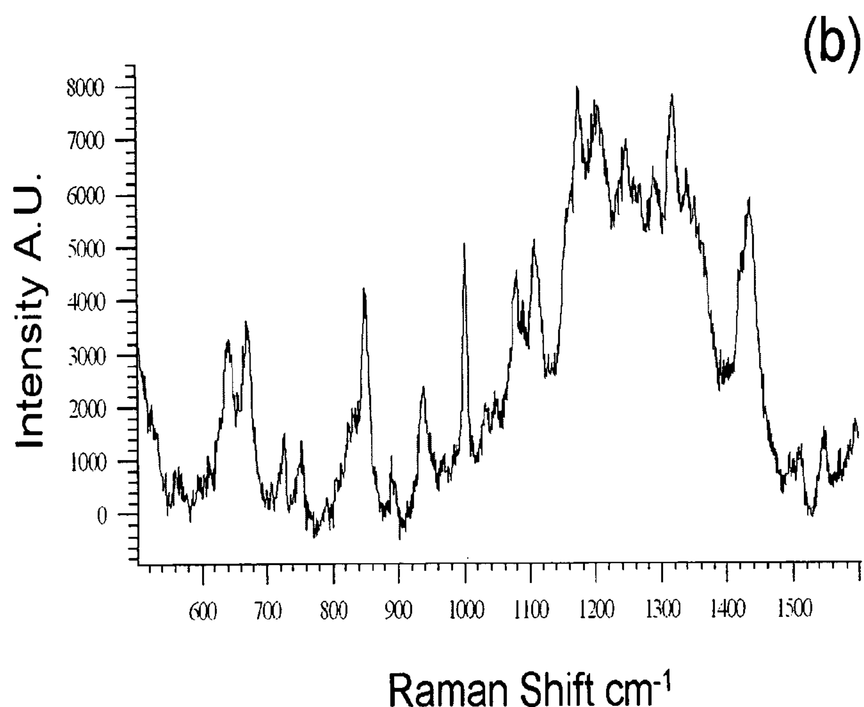
FIG. 3*b* shows a human insulin SERS spectrum obtained using a LCPCF SERS probe after the post-fabrication processing. The fiber background has been subtracted from the observed spectrum.

Before the post-fabrication processing, a sample of R6G solution was used to test the HCPCF SERS sensor's performance. The observed SERS of R6G is shown in FIG. 3(*a*), Curve B. As shown on FIG. 3*a*, curve C is a difference spectrum of curve B and curve A obtained by using the subtraction function provided by Renishaw (Renishaw PLC, Wotton-under-Edge, Gloucestershire, United Kingdom), showing the net R6G Raman signal. Similar experiments were conducted for human insulin and tryptophan solutions using the unprocessed HCPCFs. However, no SERS signals were detected through the probe, even at higher concentrations. This is because with both the hollow core and the cladding holes were filled with solution, the photonic bandgap disappeared at the excitation laser wavelength due to the reduced refractive index contrast inside and outside the holes.

With a processed LCPCF, SERS measurements were conducted for human insulin and tryptophan again. The SERS signals presented in FIGS. 3*b* and 3*c* were collected with the 785 nm laser at 3 mW and a scanning period of 20 s. The insulin SERS signal measured through the LCPCF, FIG. 3*b*, matches almost all characteristic peaks of the reference signal reported in literature.

Figure 3C:
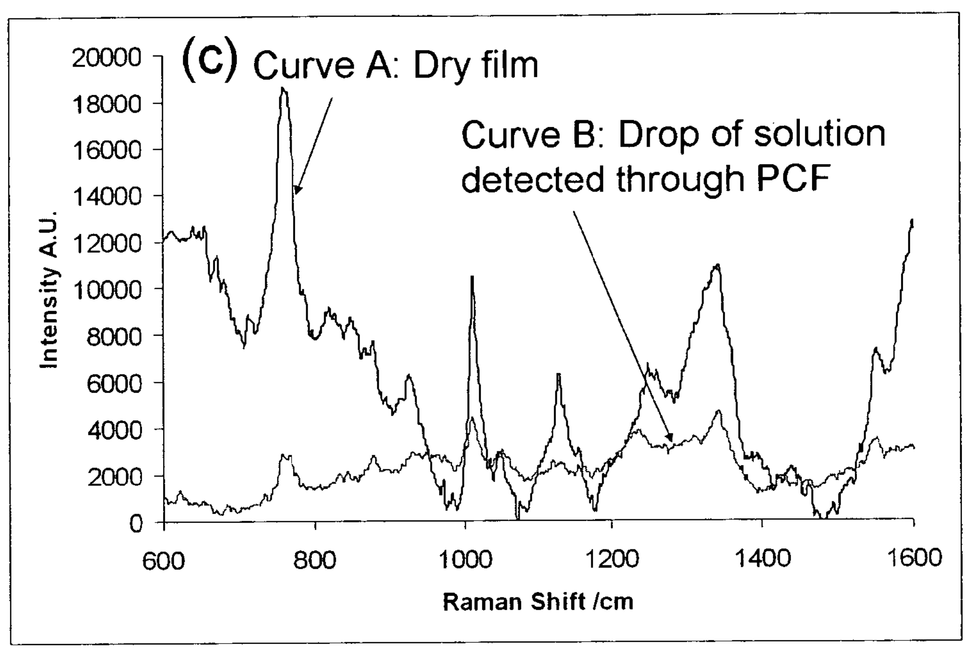
FIG. 3*c* is a comparison of SERS intensities between tryptophan obtained from the post-processed LCPCF SERS probe and that obtained directly from a dried nanoparticle/analyte film.

The SERS signal of the silver nanoparticles/tryptophan solution measured through LCPCF is shown in FIG. 3*c*, curve B. For comparison, a SERS signal from a 100 μl drop of the same solution dried on a crystal substrate was obtained. The effective size of the dried film was about 2000 $\mu m^2$, however, the laser spot size was around 200 $\mu m^2$, meaning only 1/10 of the molecules in the dried film were involved in the detection. However, in the PCF, the volume of center core was about 0.3 μl (r=3 μm and 1 cm of the central core is filled with solution). Therefore, were the molecules in the probed dry film area was 30 times that in the fiber. The Raman signal of the dried silver nanoparticles/tryptophan film is also shown in FIG. 3*c*, curve A. Clearly all the characteristic peaks match well. It is worth noticing that the magnitude of the SERS signal from the film sample is only 3 times that of the solution sample, obtained by using the curve fitting software provided by Renishaw, even though it was exposed to a laser power 10 times as strong and contained 30 times as many molecules. This gives an estimated enhancement factor ~100, introduced by the LCPCF. This enhancement is believed to result from better light confinement in the fiber core and large interaction volume between the analytes and light.

Figure 4:
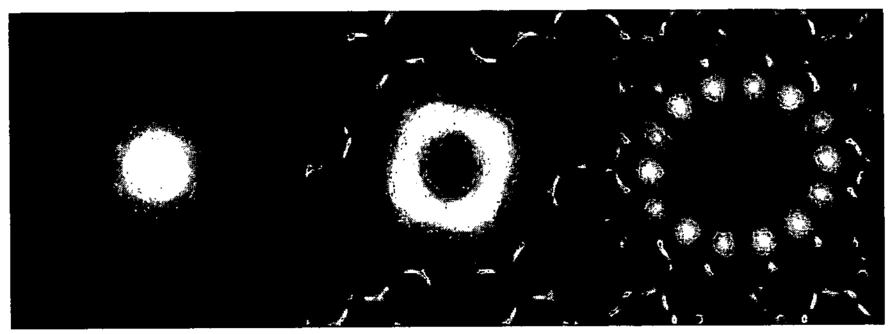
FIG. 4 shows some of the confined modes of a photonic crystal fiber (PCF) when the hollow core is empty (upper plate) or filled with liquid (lower plate).
Figure 4:
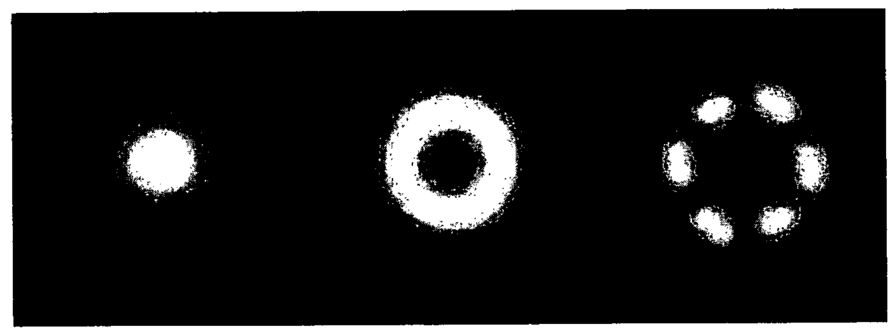

To ensure that a LCPCF can guide the laser light inside the fiber core, we studied the modes of a PCF with its hollow core filled with liquid. A theoretical analysis of the fiber modes was carried out for the HCPCF used in our experiments using the MIT photonic-bands (MPB) code. The PCF core had a diameter of 6 μm and the cladding air holes, which were arranged in a triangular lattice with a 1.6 μm pitch, had an average diameter of 1.5 μm. FIG. 4 shows some of the confined modes when the hollow core is empty or filled with liquid, respectively. The results show that when the hollow core is filled with liquid, the confinement actually becomes better, due to both the index guiding and the photonic bandgap guiding. Therefore, the theoretical simulation suggests that a LCPCF can improve the performance of the HCPCF SERS probe making it an ideal probe for sensing liquid samples.

In conclusion, a method to fabricate the LCPCF has been developed. The LCPCF sensor based on SERS has been demonstrated in the detection of molecules including R6G, human insulin, and tryptophan. With all the holes in a HCPCF filled with liquid samples, only the R6G SERS signal could be detected. However, using the LCPCF with only the hollow core filled with liquid samples, both human insulin and tryptophan SERS signals were easily detected besides R6G. This is attributed to confinement of both light and sample in the central core of the LCPCF and thereby increased interaction volume. Comparison between SERS signals measured with an LCPCF and by directly focusing the excitation light on a sample dried on a crystal substrate has indicated an enhancement factor of 100 for LCPCF. Theoretical analysis has verified the light confinement in an LCPCF.

Example II

Figure 6:
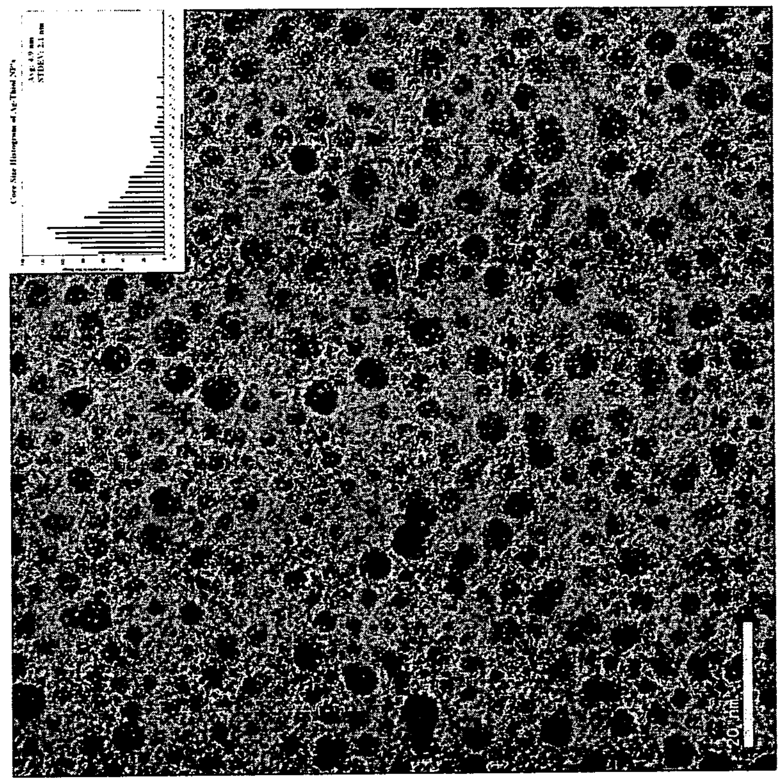
FIG. 6 is a TEM micrograph of Ag-C6SH nanoparticles. The inset shows a size histogram, illustrating an average core size for the fiber of 4.9±2.1 nm.

Synthesis of Double Substrate "Sandwich" Structure for Substrate and/or Fiber The light source was a 633 nm diode laser inside the Renishaw micro-Raman spectrometer with a Leica microscope and 50× objective. The multi-mode fiber (MMF) used as a SERS probe was purchased from Newport (Model F-MLD-500) (Newport Corporation, Irvine, Calif.). The SNPs coated on the tip passivated with hexanethiol were prepared by using a modified Brust method (Brust et al. (1994) J. Chem. Soc.-Chem. Comm. 801: 1994). Typically, 170 mg of $AgNO_3$ was dissolved in 5 ml of ethanol and kept under constant magnetic stirring. To that mixture, 3 molar equivalents of hexanethiol was added dropwise followed by an addition of 80 ml of toluene. The solution was subsequently reduced with a tenfold molar excess of $NaBH_4$ in 10 ml of nanopure water. The reduction was allowed to proceed overnight. Afterward, the solution was washed several times with nanopure water to remove any inorganic impurities and the toluene phase was collected and was placed under rotary evaporation. The particles were further purified with methanol and the resulting purified hexanethiolate-protected silver (AgC6) nanoparticles were collected on a glass frit. In order to determine the core size of the particles, transmission electron microscopy was used (National Center for Electron Microscopy, Lawrence Berkeley National Labs). The samples were (~1 mg/ml) dropcast onto a 200 mesh carbon grid. FIG. 6*a* shows a TEM micrograph of the Ag—C6SH. The average core diameter is 4.9±2.1 nm. UV-visible spectroscopic measurements of the resulting particles in tetrahydrofuran solvent exhibited an intense absorption peak at 425 nm, characteristic of the surface plasmon resonance of SNPs.

The coating of the fibers was based on a simple dipping procedure. A concentrated solution of the silver nanoparticles (10 mg/ml) was prepared. The end of the fiber, with its protection jacket removed, was then dipped into the solution and left in the solution for 5 minutes. After dipping, the end of the fiber coated with the silver particles was washed with copious amounts of ethanol and then dried with a gentle stream of ultra-high purity nitrogen. The fiber was then placed in a UVO chamber for ten minutes to remove the organic component from the particles. The dipping procedure was repeated to form a multilayer of particles on the surface of the fiber optic fiber.

The SNPs used in the solution were prepared by using a different synthetic protocol from Lee and Meisel (Lee and Meisel (1982) J. Phys. Chem. 86: 3391). Briefly, silver nitrate was used as the metal precursor and sodium citrate as the reducing agent. The formation of the SNPs was monitored by UV-vis spectroscopy using a HP 8452A spectrometer with 2 nm resolution, and the corresponding surface plasmon absorption in the aqueous solution was observed at 406 nm. The core diameter of these SNPs was found to be 25 nm by observation under a transmission electron microscope (TEM, Model JEOL JEM 1200EX). Compared to the AgC6 particles organic solvent, nanoparticles made by the Lee and Meisel method in aqueous solution have larger average diameter but show a blue shift in the plasmon peak. The reason for this seemingly contradictory data is that the peak position depends not only on particle size but also on the media or the solvent. The larger refractive index of dielectric constant of the organic solvent causes a substantial red-shift of the plasmon peak compared to that of water.

The sample solution in this study was prepared for various concentrations of R6G molecules ($10^{-5}$ M-$10^{-9}$ M) and sodium chloride (NaCl, 10 mM) was added to induce aggregate formation. Starting with aqueous R6G solution ($10^{-4}$M), SNPs was added to dilute the R6G solutions. 30 μl of the R6G solution and 270 μl of the SNPs colloid were mixed and therefore we obtained 300 μl sample with a concentration of $10^{-5}$ M of R6G molecules. Then 30 μl of the resulting solution was added to 270 μl of the SNPs colloid again to obtain a sample solution with an R6G concentration of $10^{-6}$M. Solutions of various concentrations from $10^{-7}$ M to $10^{-9}$ M, respectively, were prepared using the similar method. The solutions were incubated for about 10 minutes at room temperature and then activated with 15 μl NaCl solution. Raman tests were performed about 20 minutes after the introduction of salt.

Four different configurations were tested to compare the performance of the TCMMF sensors with other approaches, for various concentrations: 1) detection with the TCMMF probe dipped in the mixed sample solution; 2) direct detection of the SERS signal in the sample solution; 3) detection with an uncoated MMF as the probe dipped in the mixed sample solution; 4) detection with the TCMMF probe dipped in the aqueous R6G solution.

The lowest detectable concentration with the fourth configuration was around $10^{-3}$ M~$10^{-4}$ M, which was much higher than the other three methods, therefore, was not included in the following comparison.

FIGS. 7*a*, 7*b*, 7*c*, 7*d*, and 7*e* compare results obtained with the first three methods for various concentrations. For each concentration, the output power from the laser diode was 3.2 mW, and at the far end of an ordinary MMF, the power was around 3.0 mW, indicating a 93.75% coupling efficiency. Whereas at the far end of a TCMMF, the power was 1.0 mW, indicating that most of the light was absorbed by the SNPs coated at the tip and the field was confined well around the tip. The lowest detectable concentration with the last approach was around $10^{-3}$ M~$10^{-4}$ M, which was much higher than the other three methods and did not considered in this comparison. Taking the peak at 1514.3 $cm^{-1}$ as an example, the SERS intensity versus R6G concentration was shown in FIG. 7*f*.

Based on quantitative comparison of the SERS results, the lowest detectable concentration using the MMF probe, direct solution detection, and the TCMMF probe were $10^{-6}$ M, $10^{-8}$ M and $10^{-9}$ M, respectively. For the same concentration of R6G, the signal intensity from the TCMMF probe was consistently much higher than that from the MMF probe or direct solution detection, as well as the simple sum of the signals from MMF plus the direct solution detection. This indicates stronger SERS activity with the TCMMF due most likely to stronger electromagnetic enhancement as a result of the unique "sandwich" structure. Such sandwich structures formed by SNPs on the fiber probe with SNPs in solution are expected to exhibit stronger SERS due to stronger electromagnetic enhancement as compared to each substrate alone since some of the R6G analyte molecules are at junctions of SNPs. Under the same given conditions, the TCMMF experimental setup can be easily reproducible as for the practical usage. These results show that sandwich structures are indeed promising for improving SERS detection.

In conclusion, a unique double substrate sandwich structure based on TCMMF has been developed as a highly sensitive SERS probe. This probe is tested using R6G molecules and the sensitivity has been found to be 10 times better than that using a single SNPs substrate in solution. Concentration as low as $10^{-9}$ M can be readily detected using this probe, which is not possible using one of the two single substrates alone. The improvement of SERS sensitivity is attributed to the extremely large electromagnetic enhancement between SNPs. These experiments demonstrate the potential of using such a "sandwich" configuration for chemical and biological sensing and detection applications.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore; be determined with reference to the appended claims, along with the full scope of equivalents to which such claims are entitled.

We claim:

1. A process for fabricating a photonic crystal fiber, the method comprising the steps of (i) mixing $AgNO_3$ with ethanol; (ii) stirring the $AgNO_3$ in ethanol until the $AgNO_3$ is dissolved in the ethanol; (iii) adding three molar equivalents of hexanethiol to the solution; (iv) adding toluene to the solution; (v) reducing the solution using a ten-fold molar excess of $NaBH_4$ dissolved in nanopure water; (vi) washing the solution at least three times with nanopure water thereby removing inorganic impurities; (vii) collecting the toluene phase; (viii) evaporating the toluene phase, thereby causing metallic nanoparticles to come out of solution; (ix) collecting the metallic nanoparticles; (x) dissolving the metallic nanoparticles in methanol; (xi) evaporating the methanol; (xii) collecting the metallic nanoparticles; re-dissolving the metallic nanoparticles in methanol; (xiii) providing a crystal fiber, the crystal fiber having a proximal end and a distal end; (xiv) dipping the distal end of the crystal fiber into the metallic nanoparticle solution; (xv) removing the distal end of the fiber from the metallic nanoparticle solution; (xvi) washing the distal end of the crystal fiber with ethanol; (xvi) drying the distal end of the crystal fiber using a gas; (xvii) irradiating the crystal fiber with ultra-violet radiation; (xviii) repeating steps (xiv) through (xvii) at least once; the process thereby fabricating a photonic crystal fiber.

2. The process of claim 1 wherein the metallic nanoparticles are hexanethiolate-protected silver (AgC6) nanoparticles.

* * * * *